(12) United States Patent
Chen et al.

(10) Patent No.: US 6,948,387 B2
(45) Date of Patent: Sep. 27, 2005

(54) CLAMP CALIBRATION APPARATUS AND METHOD

(75) Inventors: Chong Hao Chen, Singapore (SG); Wei Liu, Singapore (SG); Ka Shing Kenny Kwan, Singapore (SG)

(73) Assignee: ASM Technology Singapore PTE LTD, Singapore (SG)

( * ) Notice: Subject to any disclaimer, the term of this patent is extended or adjusted under 35 U.S.C. 154(b) by 231 days.

(21) Appl. No.: 10/347,846

(22) Filed: Jan. 17, 2003

(65) Prior Publication Data

US 2004/0139782 A1 Jul. 22, 2004

(51) Int. Cl.⁷ .............................................. G01L 1/00
(52) U.S. Cl. .................................. 73/862.541; 73/1.08
(58) Field of Search .............................. 73/1.01, 1.08, 73/1.09, 1.11, 1.15, 1.79, 865.9, 862.541, 62.542

(56) References Cited

U.S. PATENT DOCUMENTS 4,603,395 A * 7/1986 Steinberger .................. 702/41
5,243,545 A * 9/1993 Ormond ....................... 702/88
5,929,346 A * 7/1999 Fukami ................... 73/862.541
6,505,494 B1 * 1/2003 Wollermann ................ 73/1.15

* cited by examiner

Primary Examiner—Robert Raevis
(74) Attorney, Agent, or Firm—Ostrolenk, Faber, Gerb & Soffen, LLP

(57) ABSTRACT

The invention provides an apparatus and method to calibrate a clamp, such as a wire clamp, which is suitable for use with a wire-bonding machine for semiconductor devices. A contact means is arranged to be contacted by an arm of the clamping device and a sensing mechanism is positioned in operational relationship with the arm. An indexing means is adapted to change positions of the clamping device relative to the contact means incrementally as said arm maintains contact with the contact means. The sensing mechanism is capable of sensing feedback from said arm at various positions of the clamping device relative to the contact means. The apparatus is particularly suitable for measuring a clamping force and/or a clamping gap between clamping arms of the clamping device.

27 Claims, 5 Drawing Sheets

CLAMP CALIBRATION APPARATUS AND METHOD

FIELD OF THE INVENTION

The invention relates to an apparatus and method for calibrating a clamp, such as to measure a wire clamp's clamping force and gap between clamping members for the purpose of calibration. The apparatus and method is suitable for use with a wire clamp integrated with a wire-bonding machine for semiconductor devices, but it should be appreciated that the invention is capable of wider application.

BACKGROUND AND PRIOR ART

During wire-bonding of semiconductor devices, wherein electrical connections are made between bond pads of dice and/or substrates on which they are attached, it is common to utilize a wire clamp to feed a roll of bonding wire towards a bonding site. The clamp is opened to allow wire to feed through during threading of the wire through a capillary and thereafter closed to control the wire. The wire clamp may also be used to hold the wire in position during the making of a first bond and a second bond on the die and/or substrate. The clamp is further commonly used to enable looping of a length of bonding wire between electrical contact points on the die and/or substrate, and/or to pull wires from bonds after the bonds have been made.

The clamp typically comprises a movable arm or member, and a fixed arm or member. The movable arm is opened and closed by a solenoid or a linear motor, and is usually urged towards the fixed arm by a spring or the motor. The bonding wire is very fine, to the order of 1 mil or less. Thus the wire is easily broken if subjected to excessive force. It is important that a clamping force exerted by the wire clamp is sufficient to grasp the wire, but not too high so as to cause abnormal deformation or to break the wire. It is also important that a gap between the movable and fixed arms is sufficient for the wire to pass through, and yet not be so large as compared to the size of the wire when opened so that the clamping force cannot be easily or reliably controlled.

In view of the above, it is usually necessary to calibrate a wire clamp prior to using it. Prior art devices for calibrating wire clamps have been devised, but such prior art devices involve too much human intervention and have become less effective as the diameters of bonding wires decrease together with decreasing dimensions of semiconductor packages.

For example, in order to measure clamping force, a gram gauge (see FIG. 1) has been used in the prior art. The gram gauge has a deflectable lever, which measures a deflecting force exerted on the lever by a movable wire clamp member. The gram gauge functions in much the same way as a conventional weighing scale. However, a spring which biases the lever during deflection is not sufficiently sensitive where the clamping force is small and only deflects the deflectable lever minimally.

In order to measure a gap between clamping members, a thin gauge sheet of a known thickness may be inserted between the clamping members (see FIG. 2). If the gauge sheet cannot fit into the gap, it means that the distance between the clamp members is smaller than the thickness of the gauge sheet. If the gauge sheet can fit into the gap with space to spare, then the distance is much larger than the thickness of the gauge sheet. The distance between the clamp members should be adjusted so that the gauge sheet just fits into the gap. Thus, this method is based on trial-and-error, and the error margin gets larger as the distance between clamp members (for smaller diameters of wires) gets smaller. In the event, this method does not offer sufficient accuracy for thinner wires for smaller semiconductor packages.

SUMMARY OF THE INVENTION

An object of the invention is to seek to provide a more effective apparatus and method to measure and calibrate clamping force and gap of wire clamps to cater for wires of smaller diameters as compared to the aforesaid prior art.

According to a first aspect of the invention, there is provided apparatus for calibration of a device for clamping a workpiece, comprising a sensor member adapted to sense settings of the clamping device, said sensor member providing signals relating to the settings, a monitoring device for monitoring signals emanating from the sensor member; and means to index the workpiece during calibration, wherein the monitoring device is capable of sensing feedback from the clamping device at various positions of the clamping device relative to the sensor member, whereby the clamping device is calibrated.

According to a second aspect of the invention, there is provided a method for calibration of a device for clamping a workpiece, comprising:

(i) a sensor member adapted to sense settings of the clamping device
(ii) providing signals relating to the settings from said sensor member;
(iii) a monitoring device for monitoring signals emanating from the sensor member;
(iv) means to index the workpiece during calibration; and
(v) incrementally changing the position of the clamping device relative to the sensor and sensing feedback from the clamping device at various positions of the clamping device relative to the sensor member, whereby the clamping device is calibrated.

It will be convenient to hereinafter describe the invention in greater detail by reference to the accompanying drawings, which illustrate one embodiment of the invention. The particularity of the drawings and the related description is not to be understood as superseding the generality of the broad identification of the invention as defined by the claims.

DETAILED DESCRIPTION OF THE PREFERRED EMBODIMENT OF THE INVENTION

Figure 1:
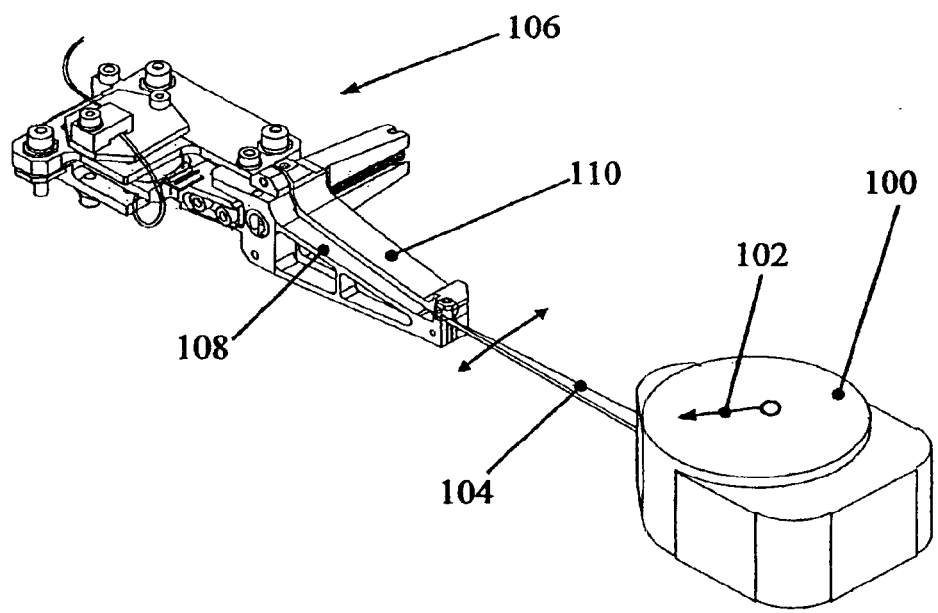
FIG. 1 is an isometric view of a gram gauge of the prior art being used to measure a clamping force of a wire clamp.

FIG. 1 shows an isometric view of a gram gauge 100 of the prior art, which comprises a deflectable lever 104 attached to a weight scale 102, being used to measure a clamping force of a wire clamp 106. The wire clamp 106 generally comprises a movable jaw or member 108 and a fixed jaw or member 110. Clamping of a wire extended between the movable member 108 and fixed member 110 is achieved by using a motor to control opening and closing of the movable member 108.

In order to measure the clamping force of the wire clamp 106, the deflectable lever 104 is placed against the movable member 108 of the wire clamp 106 in an open position while the gram gauge 100 is firmly secured. As the lever 104 is deflected by closing movement of the movable clamp member 108, the weight scale 102 displays the clamping force that is acting on the lever 104, and thus the clamping force is obtained. However, where the clamping force is relatively small, the margin of error in the gram gauge 100 increases. Also, there is a potential for measurement errors due to human error if the gram gauge 100 is not properly positioned in contact with the movable member 108. As a result, the measurements can vary and be inconsistent.

Figure 2:
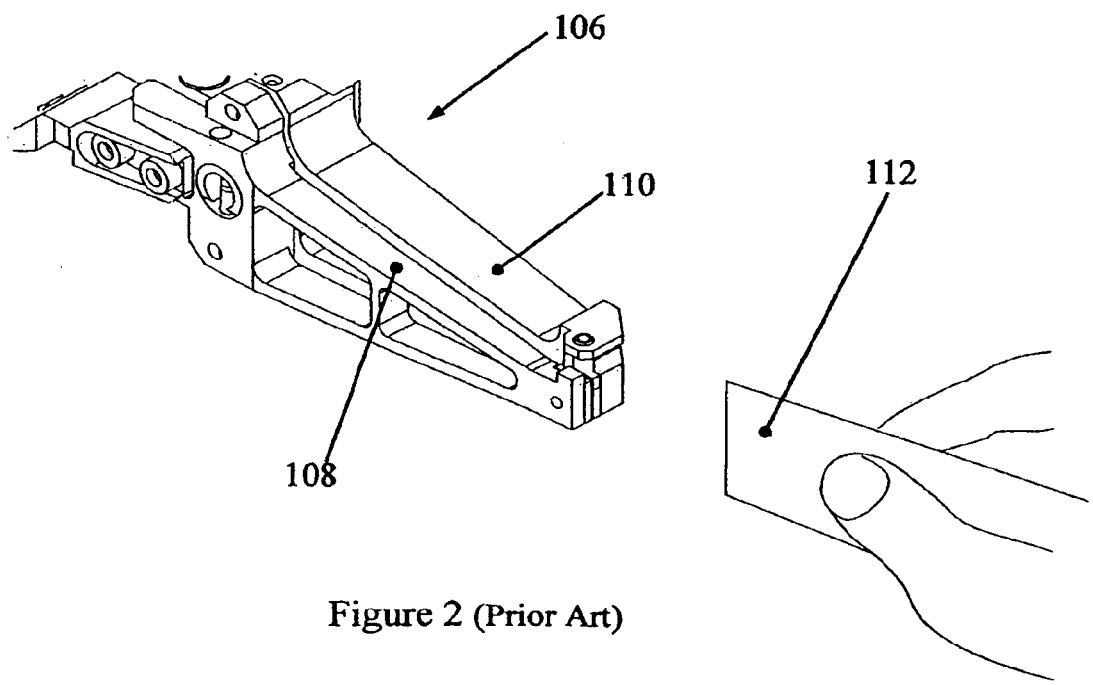
FIG. 2 is an isometric view of a gauge sheet being used to measure a gap between clamp members of a wire clamp.

FIG. 2 is an isometric view of a gauge sheet 112 being used to measure a gap between the movable clamp member 108 and fixed clamp member 110 of a wire clamp 106. In order to measure the gap, a gauge sheet 112 of known thickness is inserted between the clamp members 108, 110. If the gauge sheet 112 cannot be inserted, it means that the gap is smaller than the thickness of the gauge sheet 112 and a thinner sheet is used, until a certain thickness of gauge sheet 112 can be inserted. The size of the gap would be taken to be the thickness of the gauge sheet 112 that can be inserted.

Nevertheless, it would be appreciated that the gap measurement is at best an estimation by an operator. As with any estimation, there is a potential for inconsistent results due to human error. Moreover, it has been found that the wire clamp gap cannot be properly measured if the gap is very small (for example, if the gap is less than 2 mil). The cleanliness of surfaces of the wire clamp members 108, 110 in contact with the gauge sheet 112 may also be affected by residue from the gauge sheet 112 being left behind on these surfaces when it is forcibly inserted and removed.

Figure 3:
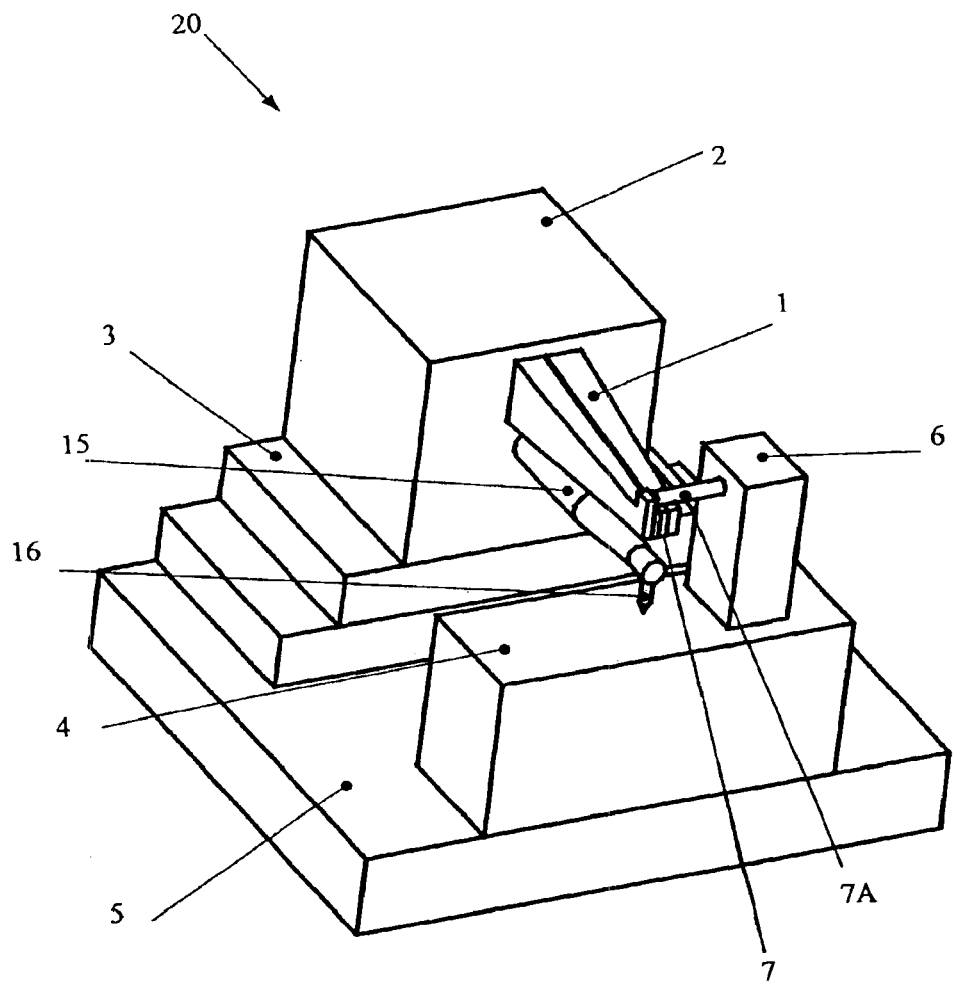
FIG. 3 is a schematic isometric representation of a sensor jig according to a preferred embodiment of the invention which is set up to measure a clamping force and gap of a wire clamp of a wire-bonding apparatus.

FIG. 3 is a schematic isometric representation of a sensor jig 6 according to a preferred embodiment of the invention which is set up to measure a clamping force and gap of a wire clamp 1 of a wire-bonding apparatus 20. The wire clamp usually includes opposed fixed and movable arms for holding the wire. Generally, the wire-bonding apparatus 20 comprises a base 5 on which is mounted a work holder 4 and an indexing means, in the form of a movable XY table 3. The work holder 4 is used to hold and position a substrate (not shown) during wire-bonding, whereas the XY table 3 is used to position a bond head 2 during wire-bonding. An ultrasonic transducer 15 and bond tip 16, and wire clamps 1, are separately attached to the bond head 2 to perform the actual wire-bonding on the substrate on the work holder 4. A sensor member in the form of a sensor jig 6 includes contact means, 7a, which may simply be a protruding member, or may also include a sensing mechanism 7 on the contact means. The sensing mechanism in this embodiment may be a contact sensor or a force sensor that is set up on the work holder 4. The contact means 7a, including the force sensor 7 (employed) is in contact with the movable member or arm of the wire clamp 1 during movement. Other sensing mechanisms can also be used. For example, where a gap of the wire clamp 1 is to be measured, a displacement sensor could be used instead, of a force sensor in a modified arrangement, as will be described in more detail below in relation to FIG. 6.

Figure 4:
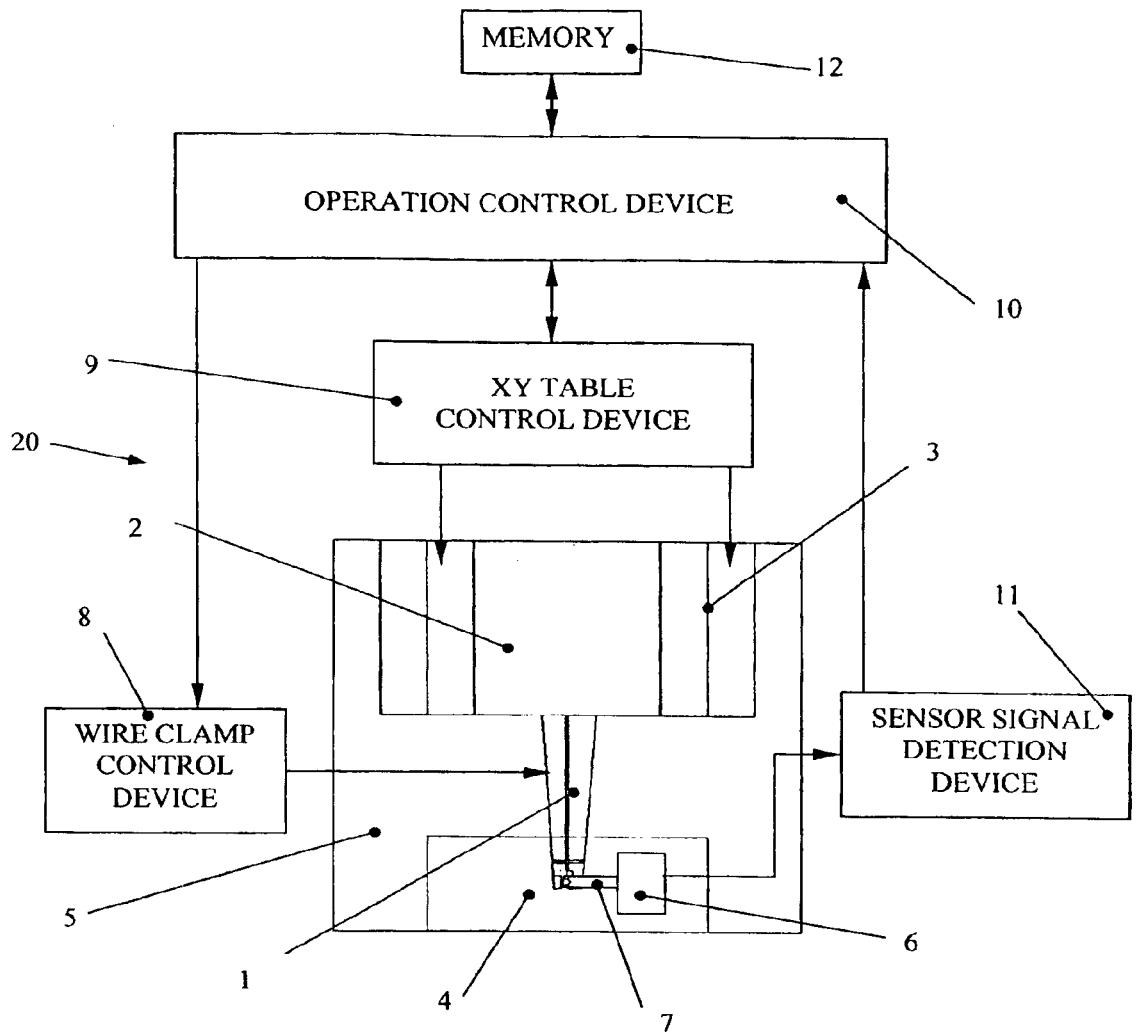
FIG. 4 is a schematic plan view of the set-up of the sensor jig in relation to the wire-bonding apparatus.

FIG. 4 is a schematic plan view of the set-up of the sensor jig 6 in relation to the wire-bonding apparatus 20. The force sensor 7 of the sensor jig 6 is in contact with a surface of the movable clamp member of the wire clamp 1 adjacent to the clamping area. The force sensor 7 is arranged such that it is perpendicular to the said contact surface of the clamp member and opposes a clamping motion of the movable clamp member.

The sensor jig 6 is connected to a monitoring device such as a sensor signal detection device 11 to provide readings of forces exerted by the moving clamp member on the force sensor 7. The opening and closing of the wire clamp 1 is controlled by a wire clamp control device 8. Movement of the XY table on a horizontal plane is controlled by an XY table control device 9. The sensor signal detection device 11, the wire clamp control device 8 and the XY table control device are operatively connected to a central operations control device 10. It is in turn connected to a memory device 12, which may consist of any type of electronic memory device, such as random-access or flash memory.

Figure 5:
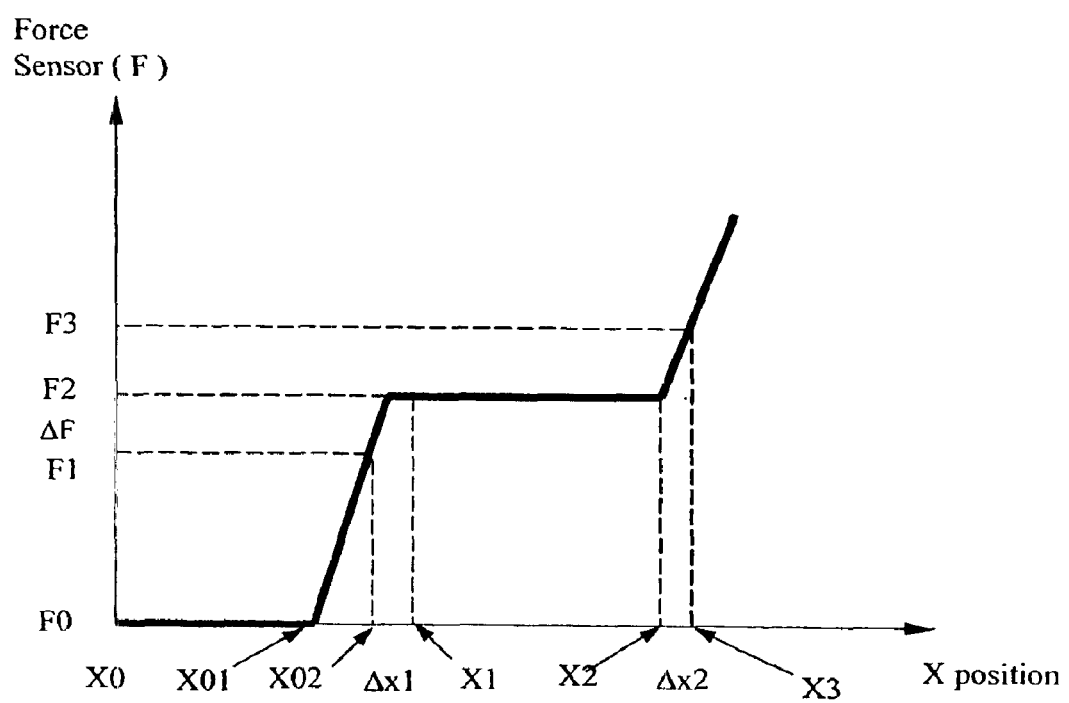
FIG. 5 is a graphical representation of a relationship between forces monitored by a force sensor as a wire clamp member is moved to bias against the force sensor for calibration of the wire clamp.

FIG. 5 is a graphical representation of a relationship between forces (F) monitored by a force sensor 7 as a movable wire clamp member is moved to bias against the force sensor 7 for calibration of the wire clamp 1. X represents positions of the XY table as the wire clamp member is moved towards the force sensor. The calibration process is now described in more detail with reference to the graphical representation in FIG. 5, showing how the force sensor can be used to simultaneously measure a clamping force and gap in a wire clamp 1.

At position X0, the movable wire clamp member is not in contact with the force sensor 7. The XY table control device 9 moves the XY table 3 towards the force sensor 7 until position X01 where the movable wire clamp member is in contact with the force sensor 7 but is not yet exerting a force on it. At this time, the movable wire clamp member of the wire clamp 1 is exerting a clamping force and is in the closed position. The XY table control device 9 moves the XY table in fixed increments (equivalent to the distances Δx1 and Δx2 in FIG. 5) towards the force sensor 7. The increments may be in the order of 0.5 μm, but the exact value depends on the sensitivity of the measurement that is desired, as will be explained below.

At position X01, the movable wire clamp member is in contact with the force sensor 7 and starts to exert an increasing force on the force sensor 7 as the moving clamp member starts to be deflected by the force sensor 7, as represented by the rising graph between X01 and X02. At each incremental position, the sensor signal detection device 11 may be programmed to sample a number of readings and the average reading of the force (F) is taken. At each position, the sensor signal detection device 11 may check for a change of the force reading ΔF beyond a certain threshold, say 0.5 grams, which indicates an equilibrium position has been reached. The threshold value will depend on the sensitivity of the force sensor 7 and other factors.

At position X02, the force measured is F1. After incrementally moving the XY table 3 by Δx1 to X1, the force measured is F2. If ΔF (F2−F1) is less than the threshold value, it means that an equilibrium position has been reached, such that the clamping force is equal to the reaction force by which the force sensor 7 is exerting on the movable wire clamp member. The clamping force F2 is thus determined.

As the XY table 3 continues to move the movable wire clamp member incrementally towards the force sensor 7, the force detected remains at F2 between positions X1 and X2, due to the equilibrium position being reached. At F3, the sensor signal detection device 11 detects that the change in force (F3−F2) is again above the threshold value. This indicates that the movable wire clamp member is now beyond its equilibrium position. The force detected by the force sensor 7 increases at a constant rate again from this point onwards.

From the graph, an operator would be able to determine the clamping force (F2) and the gap between the clamp members of the wire clamp 1 (X2−X1). As regards the sensitivity of the calibration, sensitivity can be increased by decreasing the incremental movement between positions of the XY table. This can be illustrated by the position of the graph at Δx1, wherein the equilibrium position is in fact reached in a position between X02 and X1, and not exactly at X1. If the increment Δx1 is decreased, there is a closer correlation between the position X1 and the actual position where the equilibrium position is reached.

Other measures can be taken to improve the accuracy of the reading results. For example, the force signals may be processed with a low-pass filter to remove signals that are above a certain pre-determined level, which are attributable to electronic "noise".

Another measure is to counter signal drift which may occur in certain force sensors, such as piezoelectric force sensors. For example, a certain voltage in the sensor representative of a certain pressure may be different at positions X1 and X2 due to signal drift. A solution is to measure relative peak and trough values instead of absolute values of the respective voltages at X1 and X2, so that even in the event of signal drift, the relative values can be expected to remain relatively consistent even if the absolute values are no longer the same.

Based on the two positions X1 and X2, any position within the wire clamp gap (between X1 and X2) can be fixed for conducting wire clamp force calibration. For instance, the wire clamp 1 may be fixed at the middle position of the gap (X2−X1)/2, and be driven from that point. This position may as such be used to calibrate the relationship between the position of the wire clamp 1 and the wire clamp forces. Different currents (DAC) may be used in a driving motor to drive the wire clamp 1 so as to capture the relative forces from the sensor provided by specific current values. In this way, the relationship between the motor current and the resulting force generated by a clamping member for any given wire clamp is determined.

Alternatively, if a gap of the wire clamp needs to be measured, a sensing mechanism in the form of a displacement sensor may be adopted instead of a force sensor. A displacement sensor may consist of a photoelectric sensor, a proximity sensor, a laser sensor, a vision sensor, or the like. A displacement sensor enables a position of the wire clamp member to be monitored through the sensor output. With a similar set-up as that in FIG. 3 and FIG. 4, with a protruding contract member 7*a* to bias the movable clamp member but without a force sensor (depicted as item 7), the movable clamp member can similarly be moved by protruding member 7*a*.

Figure 6:
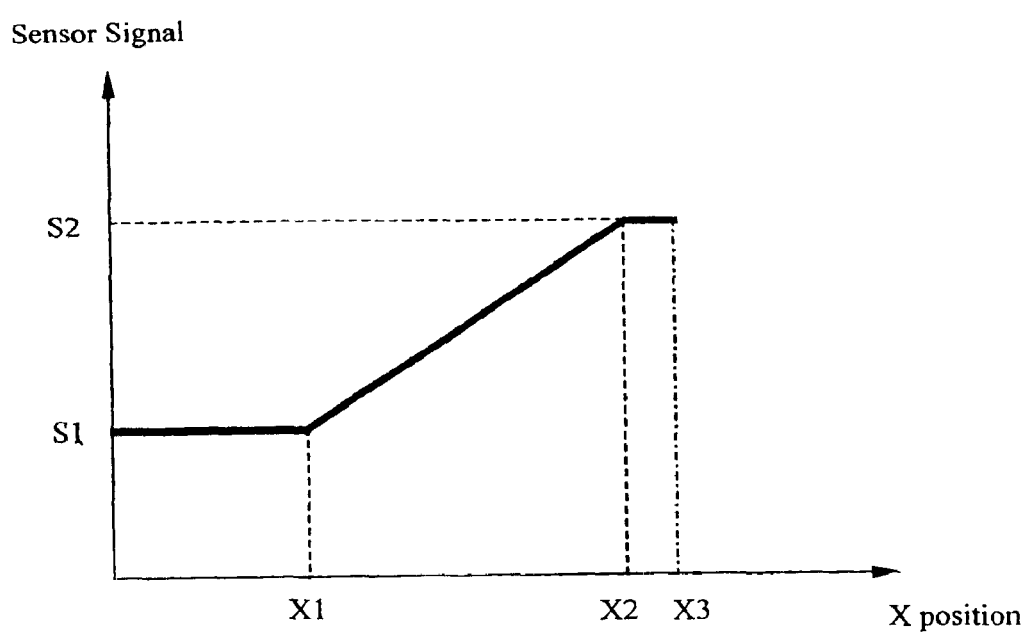
FIG. 6 is a graphical representation of a relationship between an output of a displacement sensor as a wire clamp member of a wire clamp is moved to bias against a fixed object.

As examples, a proximity sensor or a laser sensor 7B maybe placed on the side of the moving clamp member opposite the protruding member, in relatively fixed relationship to the position of the wire clamp, or a vision sensor which may comprise a CCD camera 7C may be positioned above the wire clamp members to move along with the wire clamp, to monitor movement of the moving clamp member. For simplicity, gap measurement is illustrated in FIG. 6 in graphical form, by comparing a sensor signal against the distance moved by the wire clamp. FIG. 6 is a graphical representation of a relationship between an output of a displacement sensor as a wire clamp member of a wire clamp is biased against a fixed object, such as the protruding member.

X represents positions of the XY table as the wire clamp member is moved towards the sensor, and S represents the sensor signal of say, a proximity sensor. Before position X1, the protruding member is not in contact with the moving clamp member, and thus the sensor signal remains relatively flat, since the moving clamp member is stationary. At X1, the protruding member is in contact with the moving clamp member, and starts to move the moving clamp member as the XY table 3 moves the wire clamp towards the protruding member. Thus, the sensor signal increases gradually as the moving clamp member moves closer to the displacement sensor. Then, at X2, the moving clamp member is in the fully-opened position and cannot move any closer to the displacement sensor, so that the sensor signal becomes relatively flat again. The XY table 3 may be able to displace by a further distance to X3 because of laxity, but this should not be significant. From the graph, the gap of the wire clamp 1 can be determined as the distance between X1 and X2.

The invention described herein is susceptible to variations, modifications and/or additions other than those specifically described and it is to be understood that the invention includes all such variations, modifications and/or additions which fall within the spirit and scope of the above description.

What is claimed is:

1. Apparatus for calibration of a clamping device having at least two grip arms for clamping a workpiece, comprising:
    a contact member that is arranged to be contacted by a movable grip arm of the clamping device but not by another grip arm;
    a sensor for determining a setting of the clamping device, said sensor providing signals representing the determined setting;
    a monitoring device for monitoring signals emanating from the sensor, and
    an indexing device operative to move the clamping device relative to the contact member during calibration whereby the movable grip arm is forced by the contact member to deflect relative to the other grip arm, wherein:
    the monitoring device is operative to receive signals from the sensor at various positions of the clamping device relative to the contact member, and to provide an output representative of the determined settings whereby the clamping device is calibrated.

2. Apparatus according to claim 1, wherein the indexing device is operative adapted to move the clamping device towards the contact member.

3. Apparatus according to claim 1, wherein the clamping device is a wire clamp mounted on a semiconductor wire-bonding apparatus.

4. Apparatus according to claim 3, wherein the indexing device is an XY table of the wire-bonding apparatus.

5. Apparatus according to claim 3, wherein the contact member comprises a jig coupled to a work holder for holding a semiconductor device.

6. Apparatus according to claim 1, wherein the contact member is a protruding member fixedly located in opposition to a clamping force of the movable grip arm of the clamping device.

7. Apparatus according to claim 1, wherein the sensing member comprises a sensor selected from the group consisting of: force sensor, contact sensor and displacement sensor.

8. Apparatus according to claim 7, wherein the displacement sensor comprises a sensor selected from the group consisting of: photoelectric sensor, proximity sensor, laser sensor and vision sensor.

9. Apparatus according to claim 1, wherein the setting is a force exerted by the movable grip arm of the clamping device.

10. Apparatus according to claim 1, wherein the setting is a position of the movable grip arm relative to the other grip arm not contacting the contact member.

11. Apparatus according to claim 1, wherein the sensor is located on the contact member and is configured to determine a force exerted by said movable grip arm on and the contact member.

12. Apparatus according to claim 1, wherein said indexing device is operative to move said movable grip arm of the clamping device relative to the other grip arm not contacting the contact member means incrementally as said movable grip arm maintains contact with the contact member.

13. Apparatus according to claim 1, wherein:
the clamping device is mounted on a machine; and
the monitoring device is operative to provide said output representative of the determined settings only from the sensor signals, and without reference to measurements derived from another clamping device or from operation of another machine.

14. A method for calibration of a clamping device having two cooperating grip arms for clamping a workpiece, at least one of which grip arms is movable relative to the other one, the method comprising the steps of:
contacting a first movable grip arm but not the other cooperating grip aim of the clamping device on a contact member;
indexing the clamping device by moving it incrementally so that the contact member deflects the movable grip arm relative to the other grip arm;
sensing a succession of settings of the clamping device as the movable grip arm is deflected by the contact member while the clamping device is being indexed using a sensor.
providing signals representing the succession of settings from the sensor to a monitoring device; and
operating the monitoring device to provide calibration information from the signals provided by the sensor.

15. Method according to claim 14, wherein the contact member is fixed at a certain position and the clamping device is incrementally moved towards the sensor member.

16. Method according to claim 14, including the step of determining relative positions of the clamping device and contact member whereat a force exerted by the movable grip arm on the contact member is relatively constant over a range of positions.

17. Method according to claim 16, including the step of determining a gap between the two grip arms by determining a distance over which the force exerted by the movable grip arm on the contact member is relatively constant over a range of positions.

18. Method according to claim 16, including determining a clamping force of the clamping device by determining the relatively constant force.

19. Method according to claim 16, wherein the relatively constant force is established where a change in force over an incremental distance is within a predetermined threshold value.

20. Method according to claim 14, including the step of determining a clamping gap by measuring the distance between positions whereat the grip arms are fully closed and when they are fully open while the movable grip arm is in contact with the contact member.

21. Method according to claim 14, wherein the sensor comprises a sensor selected from the group consisting of: force sensor, contact sensor and displacement sensor.

22. Method according to claim 21, wherein the displacement sensor comprises a sensor selected from the group consisting of: photoelectric sensor, proximity sensor, laser sensor and vision sensor.

23. Method according to claim 14, including locating the sensor on the contact member so as to determine a force exerted by the movable grin arm on the contact member.

24. Method according to claim 14, wherein the step of indexing the clamping device comprises the step of moving it using an XY table of a wire-bonding apparatus.

25. Method according to claim 14, including locating the contact member on a jig couple to a work holder for holding a semiconductor device.

26. Method according to claim 14, wherein:
the clamping device is mounted on a machine; and
the monitoring device is operated to provide the calibration information only from the sensor signals, and without reference to measurements derived from another clamping device or from operation of another machine.

27. Apparatus for calibration of a clamping device on a machine, the clamping device having two cooperating grip arms for clamping a workpiece, one of which grip arms is movable relative to the other grip arm, the apparatus comprising:
a contact member that is arranged to be contacted by a movable grip arm of the clamping device but not by the other cooperating grip arm;
a sensor for determining settings of the clamping device, said sensor providing signals representing the determined settings;
a monitoring device for monitoring signals emanating from the sensor; and
an indexing device to move the clamping device relative to the contact member workpiece during calibration, wherein:
the monitoring device is operative to receive signals from the sensor at various positions of the clamping device relative to the contact member, and to provide an output representative of the determined settings only from the sensor signals, and without reference to measurements derived from another clamping device or from operation of another machine.

* * * * *